United States Patent
Narciso, Jr. et al.

[19]

[11] Patent Number: 5,835,648
[45] Date of Patent: Nov. 10, 1998

[54] SURFACE ILLUMINATOR FOR PHOTODYNAMIC THERAPY

[75] Inventors: Hugh L. Narciso, Jr., Santa Barbara; Christine J. Radasky, Goleta; Daniel R. Doiron, Santa Ynez; Steven C. Anderson, Santa Barbara, all of Calif.

[73] Assignee: Miravant Systems, Inc., Santa Barbara, Calif.

Related U.S. Application Data

[60] Provisional application No. 60/012,966, Mar. 7, 1996.

[21] Appl. No.: 813,680
[22] Filed: Mar. 7, 1997
[51] Int. Cl.$^6$ ....................................................... G02B 6/26
[52] U.S. Cl. ................................ 385/31; 385/88; 362/32; 606/16
[58] Field of Search ............................. 385/31, 116, 117, 385/119, 121, 88, 901, 32, 146; 362/31, 32; 606/15, 16, 17

[56] References Cited

U.S. PATENT DOCUMENTS

| | | | |
|---|---|---|---|
| 4,991,918 | 2/1991 | Owen et al. | 385/31 |
| 5,519,534 | 5/1996 | Smith et al. | 385/31 |
| 5,708,749 | 1/1998 | Kacheria | 385/31 |

*Primary Examiner*—Hemang Sanghavi

[57] ABSTRACT

A device for delivering phototherapeutic light to uniformly illuminate a tissue surface. The device is a bowl-shaped shell with a more-or-less parabolic profile and having an open end and an apex. The inner surface of the shell is adapted to diffusely reflect light with very low absorption by the shell material. A light output end of a fiber optic is introduced into the interior of the shell through a fiber optic port in the shell wall near the apex. The light output end of the fiber is positioned such that light emanating therefrom impinges upon the inner surface of the shell. The shape of the shell causes greater than 60 percent of the light emanating from the fiber to intercept the shell's surface and be diffusely reflected. The diffusely reflected light may then undergo further diffuse reflection within the shell prior to reaching the treatment surface adjacent to the open end of the shell to provide more uniform illumination of the treatment surface than the fiber could otherwise provide. A highly reflective coating is applied to the outer surface of the shell to prevent loss of treatment light from the device. In addition, treatment light which is reflected from the tissue surface and normally lost is captured by the interior surface of the shell and re-reflected to reenter the tissue surface. Thus, little or no treatment light is lost due to reflection or scattering from tissue providing improved efficiency. The shell preferably includes a laterally extending flange around a portion of the open end which can be affixed to the tissue surface thereby preventing relative motion between the illuminator and tissue surface during treatment enabling accurate dosimetry.

16 Claims, 1 Drawing Sheet

SURFACE ILLUMINATOR FOR PHOTODYNAMIC THERAPY

BACKGROUND OF THE INVENTION

1. Field of the Invention

A device for delivering phototherapeutic light to uniformly illuminate a tissue surface.

2. Prior Art

In phototherapy in general, and in photodynamic therapy more particularly, a relatively fixed position is maintained between a treatment light source and a target tissue, so that the variation in irradiance is minimal over the treatment area. The incident irradiance is usually calculated by measuring the total power out of the light delivery system, commonly a fiber optic either alone or in a catheter, and dividing the total power by the total area exposed to the light. Irradiance is normally expressed in milliwatts per square centimeter ($mw/cm^2$) or watts per square centimeter ($w/cm^2$). In order for such calculations to be accurate, the incident irradiant light must be uniformly delivered to the treatment surface which may be highly contoured. To overcome this problem, light delivery systems have been developed to deliver light wherein the field of illumination has a uniform geometry, such as a circular, spherical or cylindrical shape. Examples include fiber optics having a microlens or a spherical diffuser, and cylindrical diffuser tips. Even though these specialized delivery systems can provide reasonably uniform output illumination, the actual distribution of light at the illuminated surface can be quite different than predicted using geometric consideration due to variations and distance of the tissue from the source. For light delivery systems not directly in contact with an illuminated treatment area, any relative movement therebetween during exposure time will greatly affect the actual fluence within the tissue and therefore the light dose delivered.

In many phototherapeutic applications it is important to provide both uniform illumination and an accurate dose of light to a target tissue area. Such phototherapies include photodynamic therapy, PUVA therapy, phototherapy for bilirubin jaundice and so forth. While it is important to apply therapeutic light uniformly to an area, it is essential to know accurately how much energy has been delivered to (entered) the tissue being treated (target tissue). Light incident upon a tissue can either penetrate into the tissue or be reflected at the tissue surface due to index of refraction differences between the tissue and the medium directly in contact with the tissue through which the treatment light must first pass to reach the tissue. Light entering the tissue can either pass through the tissue without any interaction or be absorbed by molecular election systems compressing the tissue or be scattered. If the light is scattered within the tissue such that it is transported back out of the tissue it can be viewed as light having undergone diffuse reflection.

For light in the ultraviolet yellow-orange region of the light spectrum, that is 200 nm to 600 nm, absorption is the dominant and strongest process in most tissues so that light in this spectral range generally does not penetrate tissue deeper than about 1–5 mm. For wavelengths of light in the orange to near-infrared spectrum, 600 nm to 1300 nm, spectral scattering becomes the dominant process so that this light can penetrate deeper into the tissue, typically 1–1.5 cm deep. Above 1300 nm, absorption of light by water in the tissue is strong and such longer wavelength light will not penetrate tissue. For the red or near-infrared wavelengths used in photodynamic therapy, the lightly scattering nature of the tissue makes it possible for light within the tissue to be scattered back toward the tissue surface in the direction of the light source lost from the tissue. The fluence, or space irradiance (SI), at the surface of the tissue (the total light flux incident on a square centimeter from all directions) will be the sum of both the incident irradiance and a portion of the scattered irradiance and will, therefore, be greater than the incident irradiance. It is the fluence, or SI, which is important in defining a light dose which is required for effectively administering photodynamic therapy.

The article "Light Delivery Systems for Adjunctive Intraoperative Photodynamic Therapy", by J. T. Allardice et al. in Lasers in Medical Science, 8:1–14, 1993, provides a background on the problems associated with illumination in photodynamic therapy. Allardice, et al. acknowledge the need to increase both the efficiency and uniformity of light applicators used in photodynamic therapy. They discuss the need to re-capture the light reflected from the tissue. They propose a rigid, pre-shaped applicator delivery device adapted to be attached to the tissue surface and employing integrating sphere principles to provide illumination. One of the shortcomings of their proposed device is the need for the light delivery system to have a uniform output initially so that it can be accurately positioned within the applicator to assure a uniform illumination. To date the problems associated with the loss of light from tissue due to diffuse and spectral reflection, together with the variation in and non-uniformity of illumination have not been addressed adequately.

SUMMARY OF THE INVENTION

It is an object of this invention to provide a device operable for delivering uniform illumination to a surface.

It is another object of the invention to provide a surface illuminator which can be attached to the surface being illuminated.

It is a further object of the invention to provide a surface illuminator which recaptures and utilizes scattered light from diffuse reflection.

The above object of the invention are realized by the device presented and described in more detail in the Description of the Preferred Embodiment. The device is a shell, either hollow or filled with an optically transparent material, having a substantially parabolic or bell-shaped cross-section and symmetric rotation around a central axis. The shell has an inner surface and an out surface. The inner surface is coated with a highly diffuse reflective material with a low absorption of light. The outer surface of the shell is coated with a reflecting material so that any light transmitted through the inner reflectively diffusing surface is reflected back into the interior of the shell. An output end of a fiber optic is introduced into the interior of the shell through a fiber input port disposed within the shell near the apex, opposite the open light output end of the shell. The shape of the inner surface of the shell, together with the position and light output pattern of the fiber optic tip within the shell insure that a significant portion of the light emanating from the tip of the optical fiber, greater an, intercepts the inner surface of the shell to be diffusely reflected prior to reaching the treatment surface. The diffusely reflected light may undergo multiple diffuse reflections within the shell prior to entering the tissue to provide substantially uniform illumination at the treatment surface.

Much of the light which is diffusely reflected or diffusely scattered by the tissue reenters and is captured by the interior of the shell and is re-reflected within the shell until such light eventually exits the light output end of the shell to re-enter the tissue. Thus, the device provides greater fluence at the tissue surface.

The features of the invention believed to be novel are set forth in particular in the appended claims. However, the invention itself both as to organization and method of operation, together with further objects and advantages thereof may best be understood by reference to the following description taken in conjunction with the accompanying drawings in which:

DESCRIPTION OF THE PREFERRED EMBODIMENTS

Figure 1:
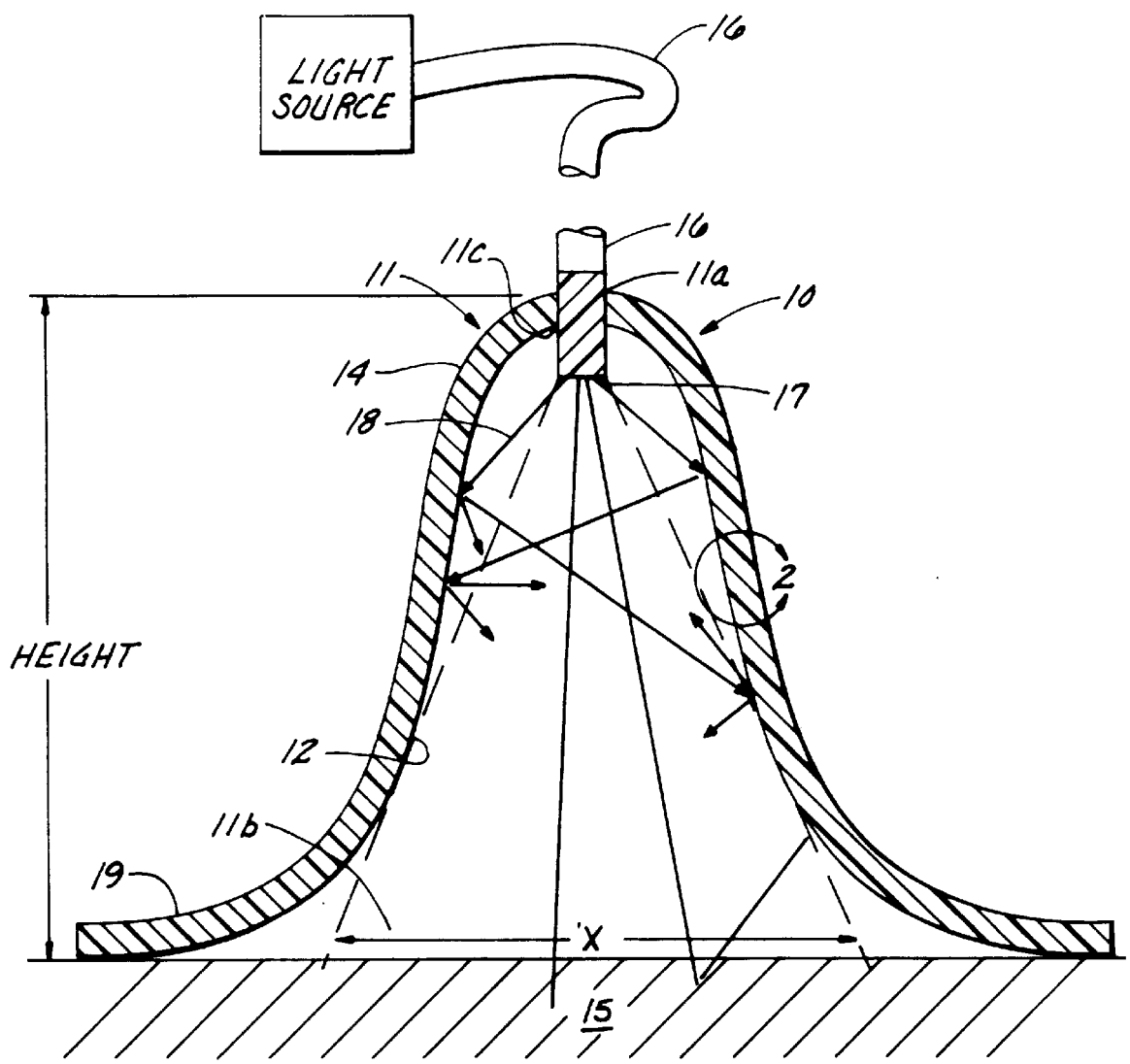
FIG. 1 is a cross-sectional view of a light delivery device in accordance with the present invention.

Turning now to FIG. 1, an embodiment of the device 10 shown in longitudinal cross-section comprises a generally bell-shaped shell 11 having a parabolic cross-sectional profile. The shell 11 has a diffusely reflective coating 12 on the inner surface thereof. The outer surface of the shell has a reflective coating 13 applied thereto. The structural material comprising the shell 11 is chosen to be substantially non-absorbing at the wavelength of light used. For PDT, red light is used and suitable materials include transparent or white plastics. The shell 11 has an apex 11a and an open light output end 11b which is, in operation, in contact with the surface of tissue 15 to be illuminated. A fiber optic 16 having a flat cut or a modified output tip 17 is introduced into the interior of the shell 11 through a fiber optic port 11c and positioned within the interior of the shell near the apex 11a so that light 18 emanating therefrom strikes an inner surface 12 of the shell 11.

Figure 2:
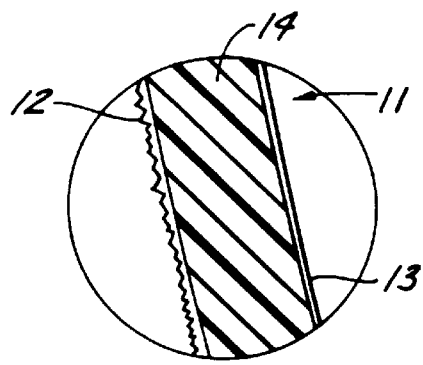
FIG. 2 is an enlarged cross-sectional view of a portion of the shell wall.

The divergent light 18 emanating from the output end of the fiber optic is multiply reflected from the diffusely reflective inner surface 12 of the shell 11 and may undergo many such reflections prior to exiting the shell 11 through the light output window 11b. Thus, the device has many of the characteristics of an integrating sphere providing uniform illumination at the light output window 11b. Light which is refracted at the inner surface enters the structural material of the shell and is reflected by the outer coating to reenter the interior of the shell. The shell wall construction is shown in enlarged detail in FIG. 2. The structural material 14 of the shell is selected to be transparent to light at the phototherapeutic wavelength.

Some of the light entering the tissue is reflected or scattered back through the tissue surface to reenter the interior of the shell 11. Upon re-entry such light from the tissue, which would normally be lost for phototherapeutic purposes, is re-reflected back into the tissue thereby increasing the fluence of light within the tissue. The device 10, in addition to being able to provide uniform illumination to a surface, is more efficient. The light that is normally lost from the surface during illumination is returned into the tissue to exert phototherapeutic effect permitting smaller doses of phototherapeutic drugs and/or light and/or shortened treatment times.

The height and the aperture width, x, of the shell 11 are chosen so that at least 60% or more of the light 18 out of the optical fiber 16 interacts with the inner surface 12 of the shell prior to reaching the skin 15 or other tissue. If the shape of the device is chosen so that the height is equal to x, that is, a half-sphere, then a fiber optic diff-user tip must be used on the input optical fiber 18 (or directly in front of the optical fiber, but not attached) to insure that a significant portion of the light interacts with the diffuse reflective inner surface 12 of the shell prior to reaching the treatment surface. The addition of a diffuser tip to the optical fiber 18 adds additional loss to the system as has been shown by Allardice, et al. ibid.

The design shown in the device at FIG. 1 was tested to determine the increased efficiency of the device and the uniformity of the illuminated surface. To determine the efficiency of the device, the device was directly compared to either the illumination of a surface by a flat cut fiber or a fiber optic with a microlens tip terminating fiber. The fluence of the tissue surface was measured using an isotropic fiber optic sensor probe supported on the tissue surface.

TABLE 1

INCREASE IN FLUENCE DUE TO APPLICATOR WITH MICROLENS AND FLAT CUT FIBER COMPARED TO FIBER DELIVERY ALONE

| DELIVERY FIBER | UNCOATED SHELL | COATED SHELL |
|---|---|---|
| Microlens | +82% | +105% |
| Flat Cut | +58% | +82% |

The uniformity of the device was also studied in comparison to the plain microlens fiber. The mean deviation with the device and without the device was 18% and 32% for the flat cut fiber respectively, and 19% and 26% for the microlens fiber. To prevent relative motion between the light output window 11b of the device 10 and the surface during treatment, the shell was formed with a flange at the base which can be easily taped or otherwise affixed to a tissue surface with a suitable adhesive. This reduces any variation in fluence with time during treatment thereby enabling delivery of an accurate dosage of light.

It is desirable to minimize the height of the device as much as possible to reduce the profile. A height of 2 to 5 cm is adequate, permitting a light delivery aperture in the shell having a diameter of up to 2 to 5 cm respectively. For a 2 cm height the practical open end diameter of the shell is preferably 1 to 1.5 cm, While particular embodiments of the present invention have been illustrated and described it would be obvious to those skilled in the art that various other changes and modifications can be made without departing from spirit and scope of the invention. For example, it is clear that the fiber optic port 11c may be disposed axially as shown in FIG. 1, or it may be disposed anywhere near the apex 11a of the shell including laterally so that the output end of a fiber optic is directed toward the central axis. The device can be either disposable or reusable. The shell may be filled with an optically transparent elastomer such as silicone. The flange 19 may extend completely around the light output window 11b or around only a portion of the perimeter. It is therefore intended to cover in the appended claims all such changes and modifications that are within the scope of this invention.

What we claim is:

1. A device adapted for attachment to a fiber optic having a light output end and to receive and enclose the light output end of the fiber optic and operable for delivering uniform illumination of light emanating from the light output end of the fiber optic to a surface comprising:

(a) a hollow, substantially bell-shaped shell having an apex and an open end and an inner surface and an outer surface;

(b) a fiber optic inlet port disposed in said shell near said apex adapted to receive the light output end of the fiber optic and immobilize said light output end to direct light emanating from said light output end to impinge upon a portion of said inner surface of said shell;

(c) a diffusely reflective coating substantially covering said inner surface of said shell;

(d) a reflective coating substantially covering said outer surface of said shell; and wherein said open end of said device is adapted to be in contact with the surface to be illuminated.

2. The device of claim 1 having a flange adapted for releasably affixing said shell to a tissue surface.

3. The device in accordance with claim 1 wherein said device further includes a fiber optic attached thereto.

4. The device in accordance with claim 2 wherein said device further includes a fiber optic attached thereto.

5. A device adapted for attachment to a fiber optic having a light output end, the device receiving and enclosing the light output end of the fiber optic and operable for delivering uniform illumination to a surface, said device comprising:

(a) a hollow bowl-shaped shell having an apex and a circular open end in opposition to said apex, said circular open end having a center and a diameter wherein said shell has a height equal to the distance between said apex and said center of said circular open end;

(b) a fiber optic inlet port disposed in said shell near said apex adapted to receive said light output end and immobilize said light output end to direct light emanating from said light output end to impinge upon a portion of said inner surface of said shell;

(c) a diffusely reflective coating substantially covering said inner surface of said shell;

(d) a reflective coating substantially covering said outer surface of said shell; and wherein said diameter of said open end is less than said height of said device, and said open end is adapted to be in contact with the surface to be illuminated.

6. The device of claim 5 wherein said shell further comprises a flange adapted for releasably affixing said shell to a tissue surface.

7. The device in accordance with claim 5 wherein said device further includes a fiber optic attached to said shell.

8. The device in accordance with claim 6 wherein said device further includes a fiber optic attached to said shell.

9. A device adapted for attachment to a fiber optic having a light output end and to receive and enclose the light output end of the fiber optic and operable for delivering uniform illumination of light emanating from the light output end of a fiber optic to a surface, said device comprising:

(a) a filled, substantially bell-shaped shell having an apex and an open end and an inner surface and an outer surface;

(b) a fiber optic inlet port disposed in said shell near said apex adapted to receive the light output end of the fiber optic and immobilize said light output end to direct light emanating from said light output end to impinge upon a portion of said inner surface of said shell;

(c) a diffusely reflective coating substantially covering said inner surface of said shell;

(d) a reflective coating substantially covering said outer surface of said shell; and wherein said open end of said device is adapted to be in contact with the surface to be illuminated.

10. The device of claim 9 having a flange adapted for releasably affixing said shell to a tissue surface.

11. The device in accordance with claim 9 wherein said device further includes a fiber optic attached thereto.

12. The device in accordance with claim 10 wherein said device further includes a fiber optic attached thereto.

13. A device for use with a fiber optic having a light output end, said device being adapted for attachment to a fiber optic having a light output end, the light output end of the fiber optic and operable for delivering uniform illumination to a surface comprising:

(a) a filled, bowl-shaped shell having an apex and a circular open end in opposition to said apex, said circular open end having a center and a diameter wherein said shell has a height equal to the distance between said apex and said center of said circular open end;

(b) a fiber optic inlet port disposed in said shell near said apex adapted to receive a fiber optic having a light output end and immobilize said light output end to direct light emanating from said light output end to impinge upon a portion of said inner surface of said shell;

(c) a diffusely reflective coating substantially covering said inner surface of said shell;

(d) a reflective coating substantially covering said outer surface of said shell; and wherein said diameter of said open end is less than said height and wherein said open end of said device is adapted to be in contact with the surface to be illuminated.

14. The device of claim 13 wherein said shell further comprises a flange adapted for releasably affixing said shell to a tissue surface.

15. The device in accordance with claim 13 wherein said device further includes a fiber optic attached to said shell.

16. The device in accordance with claim 14 wherein said device further includes a fiber optic attached to said shell.

* * * * *